United States Patent

Kanamaru et al.

Patent Number: 5,922,767
Date of Patent: Jul. 13, 1999

[54] SUBSTITUTED BENZYLUREA DERIVATIVES AND MEDICINE CONTAINING THE SAME

[75] Inventors: Yoshihiko Kanamaru, Tomisato-machi; Hiroyuki Hirota, Shisui-machi; Akihiro Shibata, Yachiyo; Teruo Komoto, Chiba; Hiroyuki Naito; Koichi Tachibana, both of Narita; Mari Ohtsuka, Narashino; Fumio Ishii, Sendai; Susumu Sato, Narita, all of Japan

[73] Assignee: SS Pharmaceutical Co., Ltd., Tokyo, Japan

[21] Appl. No.: 08/946,098

[22] Filed: Oct. 7, 1997

[30] Foreign Application Priority Data

Oct. 30, 1996 [JP] Japan .................................. 8-288216

[51] Int. Cl.$^6$ ........................ A61K 31/17; C07C 275/06; C07C 275/28

[52] U.S. Cl. ..................... 514/596; 514/357; 514/438; 514/471; 514/522; 514/534; 514/539; 514/598; 514/563; 546/286; 546/329; 549/60; 549/71; 549/72; 549/474; 549/496; 558/417; 560/39

[58] Field of Search ...................... 564/49.48, 52, 564/56; 514/596, 522, 598, 357, 471, 438, 534, 539, 563; 546/286, 329; 549/60, 71, 72, 474, 496; 558/417; 560/39; 562/463

[56] References Cited

U.S. PATENT DOCUMENTS

| 4,397,868 | 8/1983 | DeVries | 424/322 |
|---|---|---|---|
| 4,623,662 | 11/1986 | De Vries | 514/596 |
| 5,030,653 | 7/1991 | Trivedi | 514/510 |

FOREIGN PATENT DOCUMENTS 0 726 247  8/1996  European Pat. Off. .

OTHER PUBLICATIONS

Corwin Hansch, et al., vol. 64, No. 7, pp. 1186–1191, Jul. 1975, "Formulation of De Novo Substituent Constants in Correlation Analysis: Inhibition of Dihydrofolate Reductase by 2,4–Diamino–5(3,4–Dichlorophenyl)–6–Substituted Pyrimidines".

B. R. Baker, et al., Journal of Medicinal Chemistry, vol. 12, No. 1, pp. 86–88, 1969, "Irreversible Enzyme Inhibitors. CXXXVII. Active–Site–Directed Irreversible Inhibitors of Dihydrofolic Reductase Derived From 6–(ρ–Aminomethylphenoxymethyl)–2,4–Dimino–5–(3,4–Dichlorophenyl)Pyrimidine Bearing a Terminal Sulfonyl Fluoride".

B.R. Baker, et al., Journal of Medicinal Chemistry, vol. 12, No. 4, pp. 680–683, 1969, "Irreversible Enzyme Inhibitors. CLVII. Effect of Bridge Modification of the Selective Irreversible Inhibition of Dihydrofolic Reductase From L1210 Mouse Leukemia and Liver by 2, 4–Diamino–5–(3, 4–Dichlorophenyl)–6–[ρ–(M–Fluorosulfonylbenzamidomethyl)Phenoxymethyl]Pyrimidine. I".

B.R. Baker, et al., Journal of Medicinal Chemistry, vol. 12, No. 4, pp. 684–688, 1969, "Irreversible Enzyme Inhibitors. CLVIII. Effect of Bridge Modification on the Selective Irreversible Inhibition of Dihydrofolic Reductase From l1210 Mouse Leukemia and Liver by 2,4–Diamino–5–(3, 4–Dichlorophenyl)–6–[ρ–M–Fluorosulfonylbenzamidomethyl)Phenoxymethyl]Pyrimidine. II".

*Primary Examiner*—Shailendra Kumar
*Attorney, Agent, or Firm*—Oblon, Spivak, McClelland, Maier & Neustadt, P.C.

[57] ABSTRACT

Disclosed herein are substituted benzylurea derivatives represented by the following general formula (1):

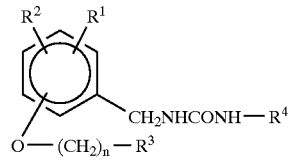

(1)

wherein $R^1$ and $R^2$ are independently H, a halogen atom, or an alkyl or alkoxyl group, $R^3$ is a phenyl or heterocyclic group which may be substituted, n is an integer of 1–6, and $R^4$ is a phenyl group which may be substituted, or salts thereof, and medicines comprising such a derivative as an active ingredient. The derivatives or salts thereof strongly inhibit only ACAT in macrophages and are hence useful as prophylactic and therapeutic agents for arteriosclerosis.

5 Claims, No Drawings

SUBSTITUTED BENZYLUREA DERIVATIVES AND MEDICINE CONTAINING THE SAME

BACKGROUND OF THE INVENTION

1. Field of the Invention

The present invention relates to novel substituted benzylurea derivatives or salts thereof, and medicines comprising such a derivative as an active ingredient, and particularly to substituted benzylurea derivatives or salts thereof, which are useful as antiarteriosclerotic agents which selectively inhibit an acyl-coenzyme A cholesterol acyltransferase (ACAT) in macrophages present in an artery wall, thereby preventing formation of foam cells, and medicines comprising such a derivative as an active ingredient.

2. Description of the Background Art

Cardiac diseases and cerebrovascular diseases stand second and third, respectively, to cancers in Japan as regards the causes of death, and are more than half the number of the causes of death if both are put together. Most of these diseases occur as a terminal symptom of arteriosclerosis. The arteriosclerosis is also caused by aging and has no general diagnosis. Besides, the name of a disease called arteriosclerosis is also not present. However, it is considered that the mortality from arteriosclerosis is very high.

With respect to the mechanism attacked by arteriosclerosis, there have been many unknown points. Many researches have been conducted in this mechanism, and the mechanism has been rapidly elucidated in recent years. More specifically, when arteriosclerosis occurs, an atherosclerotic lesion, in which cholesteryl esters are accumulated in plenty, is formed. With the growth of this lesion, the constriction of a vascular lumen progresses, resulting in complete obstruction of the vessel in the worst case. As described above, the arteriosclerosis is a very horrible disease. As a method for treating and preventing arteriosclerosis, a method of lightening risk factors dominates up to the present. This method is a method in which exacerbation factors participating in the attack of arteriosclerosis are removed. More specifically, in addition to dietetic therapy, there are many useful therapeutic and prophylactic methods such as methods of administering various kinds of serum lipid-reducing agents and antihypertensive drugs. However, the action of these drugs on arteriosclerosis is indirect, and so there is a strong demand for development of drugs which directly act on arteriosclerosis.

An ACAT inhibitor is one of the proposed drugs having such direct action. ACAT is an enzyme that acylates cholesterol to synthesize an accumulation type cholesteryl ester. In the atherosclerotic lesion in arteriosclerosis, this cholesteryl ester is accumulated in excess. It is therefore expected that the inhibition of ACAT can prevent an excess of accumulation of the cholesteryl ester, and also the growth of the sclerotic lesion.

The conventional ACAT inhibitors include compounds described in Japanese Patent Application Laid-Open Nos. 117651/1990, 234839/1992 and 7259/1991, "H. Tawara et al., J. Med. Chem., 37, 2079–2084 (1994)", and Japanese Patent Application Laid-Open Nos. 41006/1996 and 258200/1995. These documents investigate inhibitory activities against ACAT in small intestine microsomes or liver microsomes, or an action that cholesterol in plasma is indirectly reduced, but do not describe anything about inhibitory activities against ACAT in macrophages that are considered to be more important when investigating an anti-arteriosclerotic action.

Further, in compounds described in "Thomas P. Maduskuie, Jr. et al., J. Med. Chem., 38, 1067–1083 (1995)", those that more strongly inhibit ACAT in macrophages compared with ACAT in liver microsomes are also found. However, it cannot be said that their selective effects are sufficient.

SUMMARY OF THE INVENTION

Accordingly, it is an object of the present invention to provide compounds which particularly strongly and selectively inhibit ACAT in macrophages present in an artery wall among ACAT present all over the body, such as liver, gut mucosa, artery, adrenal, ovary and skin to prevent formation of foam cells, and are useful as medicines for preventing and treating arteriosclerosis.

In view of the foregoing circumstances, the present inventors have carried out an extensive investigation. As a result, it has been found that novel substituted benzylurea derivatives represented by the general formula (1), which will be described subsequently, inhibit ACAT in macrophages more strongly than ACAT in liver and are hence useful as prophylactic and therapeutic agents for arteriosclerosis, thus leading to completion of the present invention.

According to the present invention, there is thus provided a substituted benzylurea derivative represented by the following general formula (1):

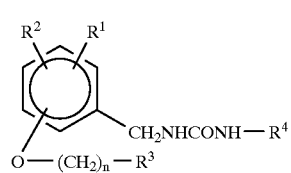

(1)

wherein $R^1$ and $R^2$ are the same or different from each other and independently represent a hydrogen or halogen atom, or an alkyl or alkoxyl group, $R^3$ is a phenyl or heterocyclic group which may be substituted, n is an integer of 1–6, and $R^4$ is a phenyl group which may be substituted, or a salt thereof.

According to the present invention, there is also provided a medicine comprising the substituted benzylurea derivative (1) or the salt thereof as an active ingredient.

According to the present invention, there is further provided a medicinal composition comprising the substituted benzylurea derivative (1) or the salt thereof and a pharmaceutically acceptable carrier.

According to the present invention, there is still further provided use of the substituted benzylurea derivative (1) or the salt thereof for a medicine.

According to the present invention, there is yet still further provided a method of preventing and treating arteriosclerosis, which comprises administering an effective amount of the substituted benzylurea derivative (1) or the salt thereof to the human or mammal.

The compounds according to the present invention selectively and strongly inhibit ACAT in macrophages and are hence useful as prophylactic and therapeutic agents for arteriosclerosis.

The above and other objects, features and advantages of the present invention will be readily appreciated as the same becomes better understood from the preferred embodiments of the present invention, which will be described subsequently in detail, and from the appended claims.

DETAILED DESCRIPTION OF THE PREFERRED EMBODIMENTS

The substituted benzylurea derivatives according to the present invention are represented by the general formula (1).

In the general formula (1), the halogen atoms of $R^1$ and $R^2$ as well as substituents on $R^3$ and $R^4$ include fluorine, chlorine, bromine and iodine atoms. The alkyl groups thereof are preferably $C_{1-6}$ alkyl groups and specifically include methyl, ethyl, n-propyl, isopropyl, n-butyl, isobutyl, sec-butyl, tert-butyl, and linear or branched pentyl and hexyl groups. The alkoxyl groups thereof are preferably $C_{1-6}$ alkoxyl groups and specifically include methoxy, ethoxy, n-propoxy, isopropoxy, n-butoxy, isobutoxy, sec-butoxy, tert-butoxy, and linear or branched pentyloxy and hexyloxy groups. Of these, the fluorine atom as the halogen atom, the methyl group as the alkyl group, and the methoxy group as the alkoxyl group are preferred.

Examples of the heterocyclic group represented by $R^3$ include furyl, thienyl, pyrrolyl, pyridyl, imidazolyl, thiazolyl, triazolyl, oxazolyl, isoxazolyl, indolyl, quinolyl and isoquinolyl groups.

Examples of substituents on the phenyl groups represented by $R^3$ and $R^4$, or the heterocyclic group represented by $R^3$ include 1–3 substituents selected from the group consisting of halogen atoms, halogenated $C_{1-6}$ alkyl groups, linear or branched $C_{1-6}$ alkoxyl groups, an amino group; mono- or di-$C_{1-6}$-alkylamino groups, a hydroxyl group, $C_{7-16}$ aralkyloxy groups, a methylenedioxy group, a cyano group, a benzoyl group, $C_{1-6}$ alkanoyl groups, a carbamoyl group, a carboxyl group, $C_{1-6}$ alkoxy-carbonyl groups, $C_{1-6}$ alkanoyloxy groups, a nitro group, a sulfonic acid group, a sulfonamide group, a thiol group, $C_{1-6}$ alkylthio groups, $C_{1-6}$ alkylsulfonyl groups, linear or branched $C_{1-6}$ alkyl groups, $C_{1-6}$ alkanoylamino groups, a benzoylamino group, hydroxy-$C_{1-6}$-alkyl groups, carboxy-$C_{1-6}$-alkyl groups, carboxy-$C_{1-6}$-alkoxyl groups and $C_{2-6}$ alkenyl groups. More specifically, examples thereof include halogen atoms; halogenated $C_{1-6}$ alkyl groups such as fluoromethyl, chloromethyl and 1,1,1-trifluoromethyl groups; $C_{1-6}$ alkoxyl groups such as methoxy and ethoxy groups; an amino group; mono-$C_{1-6}$-alkylamino groups such as monomethylamino and monoethylamino groups; di-$C_{1-6}$-alkylamino groups such as dimethylamino and diethylamino groups; a hydroxyl group; $C_{7-16}$ aralkyloxy groups such as a benzyloxy group; a methylenedioxy group; a cyano group; a benzoyl group; $C_{1-6}$ alkanoyl groups such as acetyl and propionyl groups; a carbamoyl group; a carboxyl group; $C_{1-6}$ alkoxy-carbonyl groups such as methoxycarbonyl and ethoxycarbonyl groups; $C_{1-6}$ alkanoyloxy groups such as acetyloxy and propionyloxy groups; a nitro group; a sulfonic acid group; a sulfonamide group; a thiol group; $C_{1-6}$ alkylthio groups such as methylthio and ethylthio groups; $C_{1-6}$ alkylsulfonyl groups such as methylsulfonyl and ethylsulfonyl groups; linear or branched $C_{1-6}$ alkyl groups such as methyl, ethyl, n-propyl, isopropyl, n-butyl, isobutyl, sec-butyl and tert-butyl groups; $C_{1-6}$ alkanoylamino groups such as acetylamino and propionylamino groups; a benzoylamino group; hydroxy-$C_{1-6}$-alkyl groups such as hydroxymethyl and hydroxyethyl groups; carboxy-$C_{1-6}$-alkyl groups such as carboxymethyl and carboxyethyl groups; carboxy-$C_{1-6}$-alkoxyl groups such as carboxymethoxy and carboxydimethylmethoxy groups; and $C_{2-6}$ alkenyl groups such as vinyl and allyl groups. Of these, 1–3 substituents selected from the group consisting of the halogen atoms, and the linear or branched $C_{1-6}$ alkyl groups, $C_{1-6}$ alkoxyl groups, nitro group, hydroxyl group, methylenedioxy group, mono-$C_{1-6}$-alkylamino groups, di-$C_{1-6}$-alkylamino groups, amino group and carboxyl group are preferred, with 1–3 substituents selected from the group consisting of the fluorine atom, and the methyl, isopropyl, methoxy, methylenedioxy, hydroxyl, dimethylamino and nitro groups being particularly preferred.

On the other hand, n in the general formula (1) is an integer of 1–6, with 1–4 being particularly preferred.

The substituted benzylurea derivatives (1) according to the present invention may form salts when a pyridyl, imidazolyl, thiazolyl, triazolyl, oxazolyl, isoxazolyl, quinolyl or isoquinolyl group is selected as the heterocyclic group of $R^3$, or when an amino compound, carboxylic acid, sulfonic acid or the like is substituted thereon. In this case, no particular limitation is imposed on the salts so far as they are pharmaceutically acceptable salts. Specific examples thereof include organic acid salts such as fumarates, maleates, citrates and tartrates, and inorganic acid salts such as hydrochlorides, hydrobromides and sulfates in the case where an amino compound has been substituted; and salts such as sodium salts, potassium salts and calcium salts in the case where a carboxylic acid or sulfonic acid has been substituted.

The substituted benzylurea derivatives (1) according to the present invention may be present in the form of solvates typified by hydrates.

The substituted benzylurea derivatives (1) according to the present invention can be prepared, for example, in accordance with any of the following Preparation Processes 1 to 3.

Preparation Process 1:

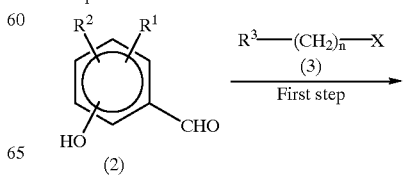

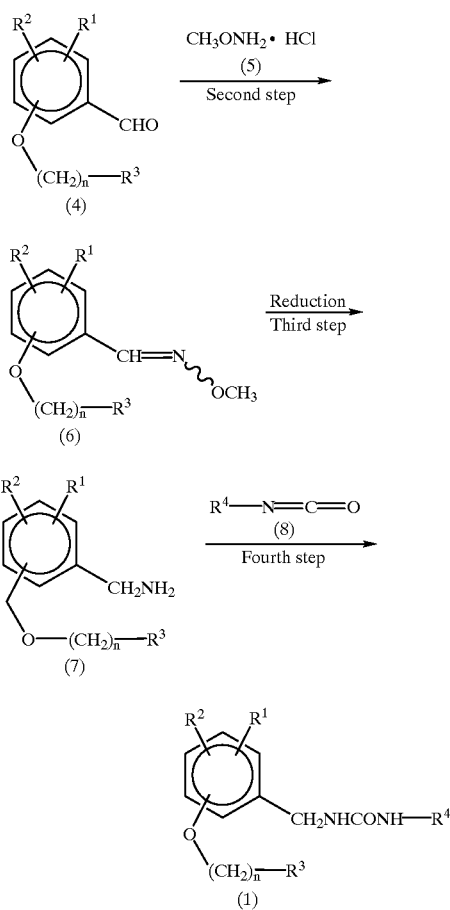

wherein R¹ to R⁴ and n have the same meanings as defined above, and X is a halogen atom.

More specifically, as shown in the above reaction scheme, a hydroxybenzaldehyde compound (2) is reacted with a halogen compound (3) (a first step), and the resultant compound (4) is reacted with a compound (5) (a second step) to obtain an O-methyloxime derivative (6). Further, the compound (6) is reduced into a benzylamine derivative (7) (a third step), and the benzylamine derivative (7) is then reacted with an isocyanate (8) (a fourth step), thereby obtaining a compound (1) according to the present invention.

The individual steps will hereinafter be described in detail.

The reaction in the first step is generally conducted in the presence of suitable base and solvent. Examples of the base used herein include sodium hydride, sodium methoxide, sodium ethoxide, potassium t-butoxide, sodium hydroxide, potassium hydroxide, sodium carbonate and potassium carbonate. No particular limitation is imposed on the solvent used herein so far as it does not affect the reaction. Examples thereof include ethers such as tetrahydrofuran, dioxane and diethyl ether; amides such as dimethylformamide, dimethylacetamide and N-methyl-α-pyrrolidone; hydrocarbons such as benzene, toluene and xylene; alcohols such as ethanol, butanol, methoxyethanol and ethoxyethanol; sulfoxides such as dimethyl sulfoxide; and ketones such as acetone an methyl ethyl ketone.

The reaction is preferably performed for 1 to 48 hours in a temperature range of from 0° C. to a temperature at which reflux occurs under heat. It is particularly preferable to conducted the reaction at room temperature for 8–24 hours by adding an equimolar amount of the halogen compound (3) to the hydroxybenzaldehyde (2) in dimethylformamide and further adding an almost equimolar amount of potassium carbonate.

The formation of the O-methyloxime in the second step is generally performed in the presence of suitable base and solvent. Examples of the base used herein include triethylamine, pyrrolidine, piperidine and pyridine. No particular limitation is imposed on the solvent used herein so far as it does not affect the reaction. Examples thereof include alcohols such as methanol and ethanol. However, pyridine of the base may be used as the solvent as it is.

The reaction is preferably performed for 1 to 24 hours in a temperature range of from 0° C. to a temperature at which reflux occurs under heat. It is particularly preferable to conducted the reaction at room temperature for 6–12 hours by using an equimolar amount of O-methylhydroxylamine monohydrochloride (5) to the benzaldehyde compound (4) in pyridine.

The reduction in the third step is preferably conducted in a hydrogen atmosphere by using an alcohol such as methanol or ethanol, adding acetic acid in an amount equal to the alcohol to dissolve the oxime compound (6) therein and then adding 10% palladium on carbon in a proportion of 5–25% by weight based on the compound (6).

The reaction is preferably performed at room temperature for 1 to 24 hours. It is particularly preferable to conducted the reaction at room temperature for 1 hour by adding 10% palladium on carbon in a proportion of 20% by weight based on the oxime compound (6) in a 1:1 mixed solvent of ethanol and acetic acid.

The reduction in the third step may also be performed by using sodium trifluoroacetoxyboron hydride [NaBH₃(OCOCF₃)]. More specifically, sodium boron hydride is suspended in tetrahydrofuran. After trifluoroacetic acid in an equimolar amount to sodium boron hydride is added to the suspension, the oxime compound (6) in a half to seventh amount as much as sodium boron hydride is added to conduct a reaction for 1–6 hours at room temperature and for 1–6 hours under heating to reflux, thereby obtaining the benzylamine derivative (7) [this synthetic procedure follows the method described in "N. Umine et al., Chem. Pharm. Bull., Vol. 26, 2897 (1978)"].

The reaction in the fourth step is performed in a suitable solvent. No particular limitation is imposed on the solvent used herein so far as it does not affect the reaction. Examples thereof include hydrocarbons such as benzene, toluene and xylene; and ethers such as ethyl ether, tetrahydrofuran and dioxane. It is particularly preferable to conduct the reaction for 1 to 24 hours at a temperature of room temperature to 150° C. by using an equimolar amount of the isocyanate (8) to the benzylamine derivative (7) and using benzene or toluene as the solvent.

Preparation Process 2:

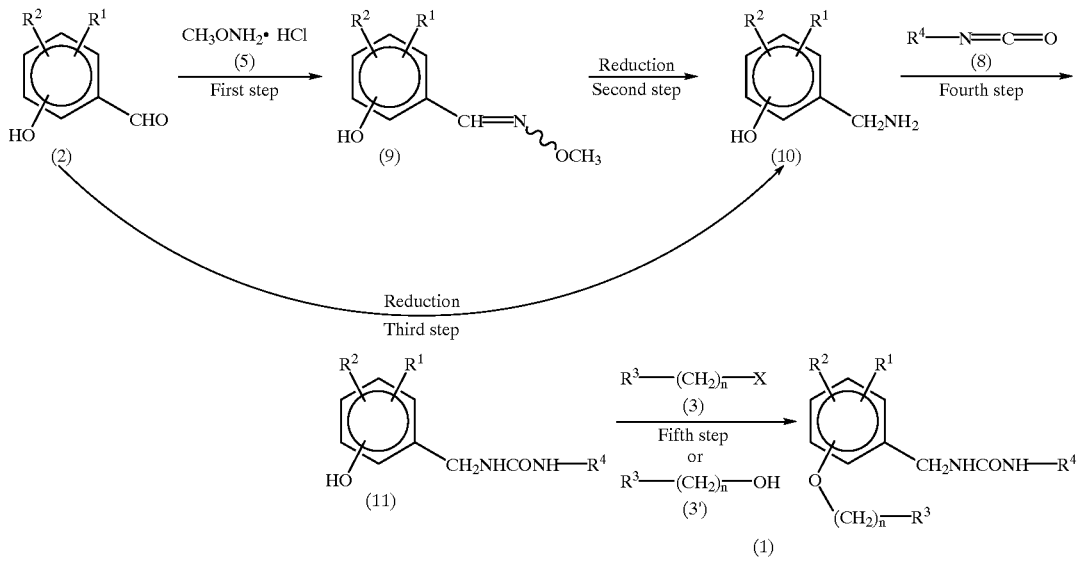

wherein $R^1$ to $R^4$ have the same meanings as defined above, and X is a halogen.

As shown in the above reaction scheme, a hydroxybenzaldehyde compound (2) is first reacted with a compound (5) (a first step) to obtain an O-methyloxime derivative (9). The compound (9) is then reduced into a benzylamine derivative (10) (a second step). Alternatively, the hydroxybenzaldehyde compound (2) may be directly reduced into the benzylamine derivative (10) (a third step). Further, the benzylamine derivative (10) is reacted with an isocyanate (8) (a fourth step) to obtain a urea derivative (11). The urea derivative (11) is then reacted with a halogen compound (3) or an alcohol (3') (a fifth step), thereby obtaining a compound (1) according to the present invention.

The individual steps will hereinafter be described in detail.

In Preparation Process 2, the synthesis in the first step may be conducted in accordance with the synthetic process in the second step of Preparation Process 1. Similarly, the syntheses in the second and fourth steps and the dehydrohalogenation reaction in the fifth step may be conducted in accordance with the synthetic processes in the third, fourth and first steps of Preparation Process 1, respectively.

The third step is preferably conducted in accordance with a process in which the hydroxybenzaldehyde compound (2) is dissolving in 10% aqueous ammonia, Raney nickel (W-2) is added in a proportion of 30% by weight based on the compound (2), and the mixture is stirred at 35–40° C. for 12 hours in a hydrogen atmosphere. By this process, the benzylamine derivative (10) can be directly obtained (this synthetic procedure follows the method described in Japanese Patent Application Laid-Open No. 310653/1993).

The dehydration condensation reaction using the alcohol (3') in the fifth step is preferably conducted under conditions for an ordinary Mitsunobu reaction. More specifically, this reaction is preferably performed in an atmosphere of an inert gas such as nitrogen or argon by using 1–2 equivalents of diethyl azodicarboxylate and triphenylphosphine as dehydration condensation agents.

No particular limitation is imposed on the solvent used herein so far as it does not affect the reaction. Examples thereof include ethers such as tetrahydrofuran and diethyl ether; and halogenated hydrocarbons such as chloroform and methylene chloride. The reaction is preferably performed at a temperature of 0–100° C. for 1 to 24 hours.

Preparation Process 3:

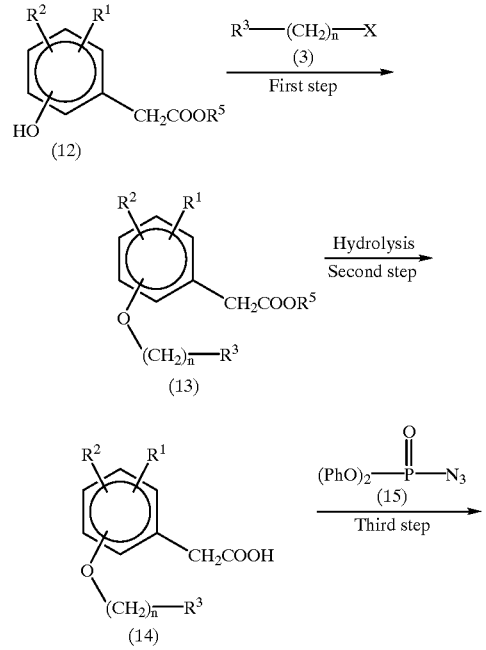

9

-continued

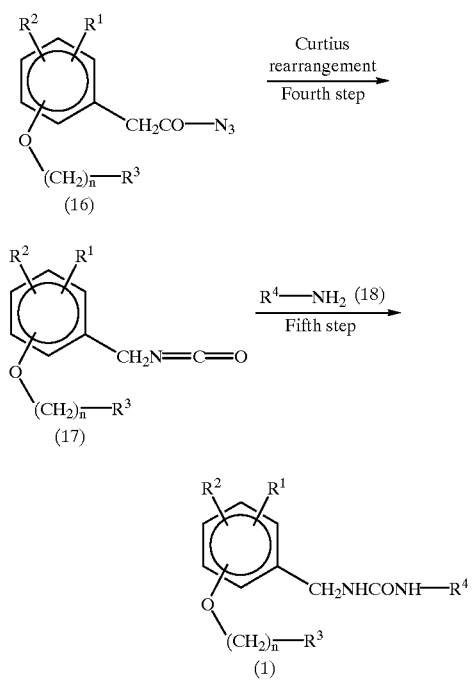

wherein $R^1$ to $R^4$ have the same meanings as defined above, and $R^5$ is a lower alkyl group.

In this process, as shown in the above reaction scheme, a halogen compound (3) is first reacted with a hydroxyphenylacetic ester (12) (a first step). The resultant compound (13) is hydrolyzed (a second step) to prepare a carboxylic acid (14). The carboxylic acid (14) is reacted with a compound (15) into an azide (16) (a third step), followed by Curtius rearrangement into an isocyanate (17) (a fourth step). The isocyanate (17) is further reacted with an amine (18) (a fifth step), thereby obtaining a compound (1) according to the present invention.

The individual steps will hereinafter be described in detail.

In Preparation Process 3, the reaction in the first step may be conducted in accordance with the synthetic process in the first step of Preparation Process 1.

The hydrolysis reaction in the second step is performed in accordance with an ordinary hydrolyzing process. More specifically, it is only necessary to conduct the reaction in a 1–10 N aqueous solution of sodium hydroxide or potassium hydroxide. In some cases, a solvent such as methanol, ethanol or dioxane may be further added due to a problem of the solubility of the compound (13). The reaction is conducted at a temperature of room temperature to 100° C. for 0.5 to 24 hours.

The azidation in the third step and the Curtius rearrangement in the fourth step are conducted by one-pot reaction without subjecting the reaction mixture to a post treatment on the way as it is. The reactions in the third and fourth steps are generally conducted in the presence of suitable base and solvent. No particular limitation is imposed on the solvent used herein so far as it does not affect the reactions. Examples thereof include hydrocarbons such as benzene, toluene and xylene.

Examples of the base include triethylamine, pyrrolidine, piperidine and pyridine, with triethylamine being most preferred.

The reactions are performed for 0.5 to 8 hours in a temperature range of from room temperature to a temperature at which reflux occurs under heat. It is particularly preferable to conduct the reactions for 1–3 hours at 80° C. under stirring by using an equimolar amount of the compound (15) to the carboxylic acid (14) in toluene and adding 1–2 equivalents of triethylamine.

The reaction in the fifth step is conducted as one pot reaction in the reaction mixture obtained in the third and fourth steps. The amino compound (18) used in the fifth step is preferably used in an amount of 1–2 equivalents to the carboxylic acid (14). The reaction is preferably performed at a temperature of room temperature to 150° C. for 1–24 hours.

The isolation and purification of the intended compound (1) in each of the above reaction schemes can be performed in accordance with a method known per se in the art, for example, by washing, extraction, recrystallization and/or chromatography. The compound (1) may also be converted into a salt or solvate in a method known per se in the art.

The thus-obtained compounds (1) according to the present invention are useful in preventing and treating arteriosclerosis, and various diseases related thereto, for example, cerebral infarction, transient ischemic attack, angina pectoris, peripheral thrombus and peripheral occlusion.

When the compound (1) according to the present invention is used as such a medicine, it is only necessary to mix the compound (1) with a solid or liquid carrier known in this technical field to prepare a medicinal composition (medicinal preparation) suitable for parenteral administration, oral administration or external administration. Examples of the medicinal preparation include liquid preparations such as injections, inhalants, syrups and emulsions, solid preparations such as tablets, capsules and granules, and external preparations such as ointments and suppositories. These preparations may contain additives usually used, such as auxiliaries, stabilizers, wetting agents, emulsifiers, absorbefacients and surfactants, as needed. Specific examples of the additives include distilled water for injection, Ringer's solution, glucose, sucrose syrup, gelatin, edible oil, cacao butter, magnesium stearate and talc.

When the compound (1) according to the present invention is used as a prophylactic and therapeutic agent for arteriosclerosis, the dose thereof varies according to the administration method thereof, and the age, weight and condition of a patient to be administered. However, it is preferable to use the compound (1) in a dose of 0.1–1,000 mg per day for an adult in the case of oral administration.

The present invention will hereinafter be described more specifically by the following Referential Examples, Examples and Test Example. However, the present invention is not limited to these examples.

Referential Example 1

Synthesis of 3-(4-nitrobenzyloxy)benzylamine:

Suspended in 160 ml of anhydrous tetrahydrofuran were 3.783 g (0.100 mol) of sodium boron hydride, and a solution of 11.402 g (0.100 mol) of trifluoroacetic acid in 20 ml of anhydrous tetrahydrofuran was added dropwise to the suspension at room temperature. The resultant mixture was stirred for 10 minutes. A solution of 5.726 g (0.02 mol) of O-methyl-3-(4-nitrobenzyloxy)benzaldoxime in 20 ml of anhydrous tetrahydrofuran was added dropwise to this mixture. The mixture was stirred at room temperature for 3 hours and heated under reflux further for 2 hours. After cooling the mixture, 20 ml of water were added under chilling with ice water, and the solvent was then distilled off under reduced pressure. The residue was extracted with chloroform, and the solvent was distilled out of the resultant extract under reduced pressure, thereby obtaining a crude product. The crude product was dissolved in 800 ml of 2 N hydrochloric acid, and the solution was washed with chloroform and then neutralized with 50% sodium hydroxide, followed by extraction with chloroform. The solvent was distilled out of the resultant extract under reduced pressure, thereby obtaining 4.234 g (yield: 82%) of the title compound.

MS (FAB, Pos.) m/z 259 (M+1).

EXAMPLE 1

Suspended in 110 ml of toluene were 2.58 g (10.0 mmol) of 3-(4-nitrobenzyloxy)benzylamine, and a solution of 2.03 g (10.0 mmol) of 2,6-diisopropylphenyl isocyanate in 10 ml of toluene was added dropwise to the suspension at room temperature. Thereafter, the mixture was heated under reflux for 1 hour. After the mixture was then allowed to cool, deposited crystals were collected by filtration, washed with toluene and then dried under reduced pressure, thereby obtaining 3.90 g (yield: 84.6%) of the intended compound, 1-(2,6-diisopropylphenyl)-3-[3-(4-nitrobenzyloxy)benzyl]urea (Compound 1), as colorless crystals. The data of Compound 1 are shown in Table 1.

Referential Example 2

Synthesis of 1-(2,6-diisopropylphenyl)-3-(3-hydroxy-4-methoxybenzyl)urea:

Added to 40 ml of toluene were 600 mg (3.92 mmol) of 3-hydroxy-4-methoxybenzylamine and 810 mg (3.90 mmol) of 2,6-diisopropylphenyl isocyanate, and the mixture was stirred under reflux for 8 hours.

After cooling the reaction mixture, deposited crystals were collected by filtration, washed with ether and then air-dried, thereby obtaining 1.03 g (yield: 74.1%) of the intended compound as crystals.

MS (FAB, Pos.) m/z 357 (M+1).

EXAMPLE 2

Added to 15 ml of dimethylformamide were 270 mg (0.758 mmol) of 1-(2,6-diisopropylphenyl)-3-(3-hydroxy-4-methoxybenzyl)urea, 160 mg (0.804 mmol) of 1-bromo-3-phenylpropane and 250 mg (1.81 mmol) of potassium carbonate, and the mixture was stirred at room temperature for 24 hour. After dimethylformamide in the resultant reaction mixture was distilled off under reduced pressure, the residue was dissolved in chloroform, and the solution was washed with water and then dried over anhydrous sodium sulfate. Further, chloroform was distilled out of the dried product under reduced pressure. Deposited crystals were ground with ether and then collected by filtration, thereby obtaining 263 mg (yield: 73.3%) of the intended compound, 1-(2,6-diisopropylphenyl)-3-[4-methoxy-3-(3-phenylpropoxy)benzyl]urea (Compound 8), as colorless crystals. The data of Compound 8 are shown in Table 2.

Referential Example 3

Synthesis of 4-(4-nitrobenzyloxy)phenylacetic acid:

After 3.15 g (10.0 mmol) of ethyl 4-(4-nitrobenzyloxy) phenylacetate were dissolved in a mixed solvent of 50 ml of methanol and 50 ml of 1,4-dioxane, 70 ml of a 1 N aqueous solution of sodium hydroxide were added, and the resultant mixture was stirred at room temperature for 2 hours. After completion of the reaction, the reaction mixture was acidified with diluted hydrochloric acid and extracted with chloroform. The resultant extract was then dried over anhydrous sodium sulfate. After distilling off chloroform under reduced pressure, deposited crystals were ground with ether, thereby obtaining 2.64 g (yield: 92.0%) of the intended compound as crystals.

MS (FAB, Pos.) m/z 288 (M+1).

EXAMPLE 3

Added to a mixture of 350 mg (1.22 mmol) of 4-(4-nitrobenzyloxy)phenylacetic acid, 340 mg (1.24 mmol) of diphenylphosphorylazide and 30 ml of toluene were 0.50 ml (3.59 mmol) of triethylamine. The resultant mixture was stirred for 3 hours at an internal temperature of 80° C. Then, 250 mg (1.41 mmol) of 2,6-diisopropylamine were added to the reaction mixture, and the mixture was stirred for 6 hours at the same temperature. After cooling the reaction mixture, toluene in the reaction mixture was distilled off under reduced pressure. After the residue was dissolved in a mixed solvent of chloroform and methanol, the solution was washed with water and dried over anhydrous sodium sulfate. After distilling off chloroform under reduced pressure, the residue was subjected to column chromatography on silica gel. A chloroform-eluted fraction was concentrated under reduced pressure, thereby obtaining 194 mg (yield: 34.5%) of the intended compound, 1-(2,6-diisopropylphenyl)-3-[4-(4-nitrobenzyloxy)benzyl]urea (Compound 17), as colorless crystals. The data of Compound 17 are shown in Table 5.

EXAMPLE 4

In a nitrogen gas atmosphere, 356 mg (1.00 mmol) of 1-(2,6-diisopropylphenyl)-3-(4-hydroxy-3-methoxybenzyl) urea, 147 mg (1.50 mmol) of 3-furylmethyl alcohol and 393 mg (1.50 mmol) of triphenylphosphine were dissolved in 20 ml of THF (tetrahydrofuran). A solution of 261 mg (1.50 mmol) of diethyl azodicarboxylate in 5 ml of THF was added dropwise to the solution at room temperature under stirring. After the mixture was stirred for 4 hours, the reaction mixture was concentrated under reduced pressure, and the residue was subjected to column chromatography on silica gel. A fraction eluted with chloroform-methanol (100:1) was concentrated under reduced pressure, thereby obtaining 409 mg (yield: 93.6%) of the intended compound, 1-(2,6-diisopropylphenyl)-3-[4-(3-furylmethyloxy)-3-methoxy benzyl]urea (Compound 33), as colorless crystals. The data of Compound 33 are shown in Table 9.

EXAMPLE 5

Dissolved in 5 ml of dioxane and 5 ml of methanol were 252 mg (0.50 mmol) of 1-(2,6-diisopropylphenyl)-3-[3-methoxy-4-(4-methoxycarbonylbenzyloxy)benzyl]urea (Compound 27). Further, 3 ml of a 1 N aqueous solution of sodium hydroxide were added to the solution, and the mixture was stirred at room temperature for 4 hours. The pH of reaction mixture was then adjusted to pH 3–4 with 2 N hydrochloric acid. The solvent was then distilled off under reduced pressure, and the resultant residue was extracted with chloroform. After the chloroform extract was filtered, the solvent was distilled out of the filtrate under reduced pressure, thereby obtaining 238 mg (yield: 97.0%) of the intended compound, 1-(2,6-diisopropyl-phenyl)-3-[4-(4-carboxybenzyloxy)-3-methoxybenzyl]urea (Compound 34), as colorless crystals. The data of Compound 34 are shown in Table 9.

EXAMPLES 6–36

Compounds 2–7, Compounds 9–16, Compounds 18–32, and Compounds 35 and 36 were prepared in the same manner as in Example 1, 2, 3 or 4. The data of the above compounds are shown in Tables 1 to 10.

| Compound No. | $R^3$—$(CH_2)_n$—O— with $R^1$, $R^2$ | $R^4$ | Melting Point (°C) | MS (FAB, Pos.) | $^1$H-NMR data (CDCl$_3$, δ) |
|---|---|---|---|---|---|
| 1 | 4-methylphenyl-O-CH$_2$-(4-nitrophenyl) | 2,6-diisopropyl-3-methylphenyl | Colorless crystal (197–198) | 462 | 1.15(d, 12H), 3.29(m, 2H), 4.36(d, 2H), 4.40–4.60(br, 1H), 5.12(s, 2H), 5.97(s, 1H), 6.80–6.90(m, 3H), 7.10–7.40(m, 5H), 7.58(d, 2H), 8.24(d, 2H) |
| 2 | 4-methylphenyl-O-CH$_2$-(4-nitrophenyl) | 2,4-difluorophenyl | Colorless crystal (203–205) | 414 | 4.39(s, 2H), 5.17(s, 2H), 6.77–6.90(m, 2H), 6.94(d, 2H), 7.26(dd, 2H), 7.61(d, 2H), 7.90–8.15(m, 2H), 8.22(d, 2H) |
| 3 | 2-methoxy-4-methylphenyl-O-CH$_2$-phenyl | 2,4-difluorophenyl | Colorless crystal (181–182) | 399 | 3.87(s, 3H), 4.25–4.40(m, 2H), 5.15(s, 2H), 6.70–7.60(m, 10H), 7.90–8.20(m, 1H) |
| 4 | 3-methoxy-4-methylphenyl-O-CH$_2$-(4-nitrophenyl) | 2,4-difluorophenyl | Colorless crystal (205–207) | 444 | 3.89(s, 3H), 4.20–4.40(m, 2H), 5.24(s, 2H), 6.70–8.40(m, 10H) |

-continued

| Compound No. | R¹, R², R³—(CH₂)ₙ—O— (structure) | R⁴ | Melting Point (°C.) | MS (FAB, Pos.) | ¹H-NMR data (CDCl₃, δ) |
|---|---|---|---|---|---|
| 5 | CH₃O-phenyl-O-CH₂-phenyl-NO₂ | 2,6-di-tert-butyl-4-methylphenyl | Colorless crystal (171–172) | 492 | 1.12(d, 12H), 3.24(m, 2H), 3.85(s, 3H), 4.27(d, 2H), 4.43(br, 1H), 5.17(s, 2H), 5.74(s, 1H), 6.81(s, 1H), 6.83(d, 2H), 7.16(d, 2H), 7.30(t, 1H), 7.61(d, 2H), 8.23(d, 2H) |
| 6 | CH₃O-phenyl-O-CH₂-phenyl | 2,6-di-tert-butyl-4-methylphenyl | Colorless crystal (190–191) | 447 | 1.13(d, 12H), 3.26(m, 2H), 3.84(s, 3H), 4.28(d, 2H), 4.40(br, 1H), 5.06(s, 2H), 5.75(s, 1H), 6.77(s, 1H), 6.80(d, 2H), 7.16(d, 2H), 7.27–7.45(m, 6H) |
| 7 | CH₃O-phenyl-O-CH₂-pyridyl | 2,6-di-tert-butyl-4-methylphenyl | Colorless crystal (177–178) | 448 | 1.13(d, 12H), 3.26(m, 2H), 3.83(s, 3H), 4.29(d, 2H), 4.46(br, 1H), 5.07(s, 2H), 5.77(s, 1H), 6.80(s, 1H), 6.84(d, 2H), 7.17(d, 2H), 7.30(m, 2H), 7.79(dt, 1H), 8.57(dd, 1H), 8.68(d, 1H) |
| 8 | CH₃O-phenyl-O-(CH₂)₃-phenyl | 2,6-di-tert-butyl-4-methylphenyl | Colorless crystal (131–132) | 475 | 1.12(d, 12H), 2.14(m, 2H), 2.80(t, 2H), 3.25(m, 2H), 3.83(s, 3H), 3.97(t, 2H), 4.28(d, 2H), 4.40(br, 1H), 5.72(s, 1H), 6.74(m, 3H), 7.12–7.32(m, 8H) |

-continued

| Compound No. | R³—(CH₂)ₙ—O—[phenyl with R¹, R²]— | R⁴ | Melting Point (°C.) | MS (FAB, Pos.) | ¹H-NMR data (CDCl₃, δ) |
|---|---|---|---|---|---|
| 9 | 4-methylphenyl-O-(CH₂)₂-O-(2-methoxyphenyl) | 2,6-di-tert-butyl-4-methylphenyl | Colorless crystal (133–134) | 461 | 1.11(d, 12H), 3.14(t, 2H), 3.24(m, 2H), 3.82(s, 3H), 4.14(t, 2H), 4.29(d, 2H), 4.42(br, 1H), 5.71(s, 1H), 6.75(m, 3H), 7.14(d, 2H), 7.29(m, 6H) |
| 10 | 4-methylphenyl-O-CH₂-(2-methoxyphenyl with benzyl substituent) | 2,6-di-tert-butyl-4-methylphenyl | Colorless crystal (193–195) | 447 | 1.13(d, 12H), 3.00–3.50(m, 2H), 3.83(s, 3H), 4.31(br.s, 2H), 4.40–4.70(m, 1H), 5.10(s, 2H), 6.01(br.s, 1H), 6.60–6.90(m, 3H), 7.00–7.50(m, 8H) |
| 11 | 4-methylphenyl-O-CH₂-(2,4-difluorophenyl with methoxy) | 2,6-di-tert-butyl-4-methylphenyl | Colorless crystal (186–187) | 483 | 1.14(d, 12H), 3.27(m, 2H), 3.83(s, 3H), 4.30(d, 2H), 4.43(br, 1H), 5.06(s, 2H), 5.72(s, 1H), 6.79(s, 2H), 6.85(s, 1H), 6.85(m, 2H), 7.17(d, 2H), 7.30(t, 1H), 7.49(m, 1H) |
| 12 | 4-methylphenyl-O-CH₂-(methoxyphenyl)-(4-methylphenyl) | 2,6-di-tert-butyl-4-methylphenyl | Colorless crystal (176–177) | 461 | 1.13(d, 12H), 2.35(s, 3H), 3.26(m, 2H), 3.82(s, 3H), 4.27(d, 2H), 4.43(br, 1H), 3.83(s, 3H), 4.27(d, 2H), 4.43(br, 1H), 5.02(s, 2H), 5.73(s, 1H), 6.77(s, 2H), 6.83(s, 1H), 7.16(d, 4H), 7.28(t, 1H), 7.31(d, 2H) |

-continued

| Compound No. | R³—(CH₂)ₙ—O— (with R¹, R²) | R⁴ | Melting Point (°C.) | MS (FAB, Pos.) | ¹H-NMR data (CDCl₃, δ) |
|---|---|---|---|---|---|
| 13 | 4-methyl-2-(4-methoxybenzyloxy)phenyl with CH₃O | 2,6-di-tert-butyl-methylphenyl | Colorless crystal (183–184) | 477 | 1.14(d, 12H), 3.26(m, 2H), 3.81(s, 3H), 3.82(s, 3H), 4.28(d, 2H), 4.42(br, 1H), 4.99(s, 2H), 5.74(s, 1H), 6.76(s, 2H), 6.85(s, 1H), 6.89(d, 2H), 7.16(d, 2H), 7.30 (t, 1H), 7.35(d,2H) |
| 14 | 4-methyl-2-(4-nitrobenzyloxy)phenyl with CH₃O | 2,6-di-tert-butyl-methylphenyl | Colorless crystal (180–181) | 492 | 1.13(d, 12H), 3.00–3.50(m, 2H), 3.85(s, 3H), 4.30–4.60(m, 3H), 5.19(s, 2H), 5.90(br.s, 1H), 6.60–7.00(m, 3H), 7.10–7.50(m, 3H), 7.58(d, 2H), 8.22(d, 2H) |
| 15 | 4-methyl-2-(4-nitrobenzyloxy)phenyl | 2,6-di-tert-butyl-methylphenyl | Colorless crystal (156–157) | 462 | 1.08(s, 12H), 3.22 (m, 2H), 4.46(d, 2H), 4.69(br, 1H), 5.01(s, 2H), 5.71(s, 1H), 6.78(t, 1H), 6.94( t, 1H), 7.13(d, 2H), 7.18(t, 1H), 7.26(m, 2H), 7.35(d, 2H), 8.18(d, 2H) |
| 16 | 4-methyl-2-(3-phenylpropoxy)phenyl with CH₃O | 2,6-di-tert-butyl-methylphenyl | Colorless crystal (153–154) | 475 | 1.15(d, 12H), 1.95–2.30(m, 2H), 2.81(t, 2H), 3.05–3.50(m, 2H), 3.82(s, 3H), 3.97(t, 2H), 4.30–4.60(m, 3H), 6.01(br, 1H), 6.65–6.85(m, 3H), 7.10–7.40(m, 8H) |

-continued
| Compound No. | R³—(CH₂)ₙ—⟨R¹,R²⟩—O— | R⁴ | Melting Point (°C.) | MS (FAB, Pos.) | ¹H-NMR data (CDCl₃, δ) |
|---|---|---|---|---|---|
| 17 | 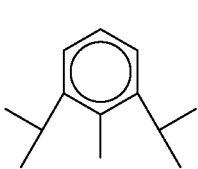 | 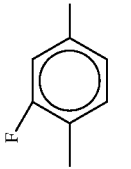 | Colorless crystal (198–200) | 462 | 1.13(d, 12H), 3.27(m, 2H), 4.32(d, 2H), 4.45(br, 1H), 5.14(s, 2H), 5.73(s, 1H), 6.86(d, 2H), 7.17(d, 4H), 7.31(t, 1H), 7.58(d, 2H), 8.23(d, 2H) |
| 18 | 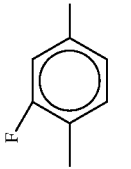 | 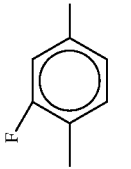 | Colorless crystal (218–220) | 414 | 4.53(d, 2H), 5.24(s, 2H), 6.32(t, 1H), 6.38(br, 1H), 6.80(m, 2H), 6.88(d, 1H), 6.99(t, 1H), 7.24(m, 1H), 7.36(m, 1H), 7.64(d, 2H), 8.00(m, 1H), 8.24(d, 2H) |
| 19 | 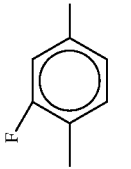 | 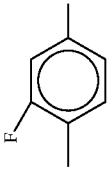 | Colorless crystal (222–224) | 414 | 4.36(d, 2H), 5.18(s, 2H), 6.33(t, 1H), 6.38(br, 1H), 6.81(m, 2H), 6.93(d, 2H), 7.27(d, 2H), 7.62(d, 2H), 8.03(m, 1H), 8.25(d, 2H) |
| 20 | 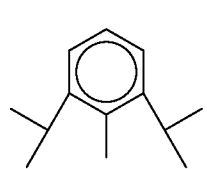 | 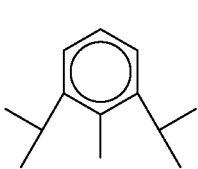 | Colorless crystal (184–185) | 483 | 1.13(d, 12H), 3.10–3.50(m, 2H), 3.83(s, 3H), 4.34(s, 2H), 4.30–4.55(t-like, 1H), 5.10(s, 2H), 5.76(br.s, 1H), 6.70–7.00(m, 4H), 7.05–7.60(m, 5H) |

-continued

| Compound No. | R¹, R², R³—(CH₂)ₙ—O— (phenyl with methyl) | R⁴ | Melting Point (°C.) | MS (FAB, Pos.) | ¹H-NMR data (CDCl₃, δ) |
|---|---|---|---|---|---|
| 21 | 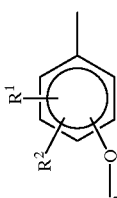 (4-Cl-C₆H₄-CH₂-O- with CH₃ and OCH₃) |  (2,6-di-tert-butyl-4-methylphenyl) | Colorless crystal (171–172) | 481 | 1.13(d, 12H), 3.00–3.50(m, 2H), 3.83(s, 3H), 4.32(br.s, 2H), 4.30–4.50(t-like, 1H), 5.06(s, 2H), 6.60–6.90(m, 3H), 7.10–7.50(m, 7H) |
| 22 | 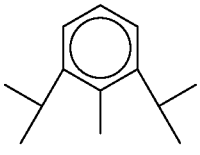 (4-CH₃O-C₆H₄-CH₂-O- with CH₃ and OCH₃) | (2,6-di-tert-butyl-4-methylphenyl) | Colorless crystal (166–167) | 477 | 1.13(d, 12H), 3.10–3.50(m, 2H), 3.80(s, 6H), 4.20–4.30(d-like, 2H), 4.30–4.50(t-like, 1H), 5.02(s, 2H), 5.90(br.s, 1H), 6.80–7.00(m, 5H), 7.00–7.40(m, 5H) |
| 23 | 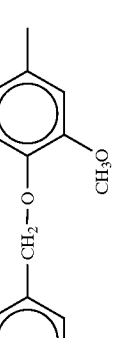 (4-NC-C₆H₄-CH₂-O- with CH₃ and OCH₃) | (2,6-di-tert-butyl-4-methylphenyl) | Colorless crystal (178–179) | 472 | 1.13(d, 12H), 3.00–3.50(m, 2H), 3.84(s, 3H), 4.20–4.40(d-like, 2H), 4.40–4.60(t-like, 1H), 5.15(s, 2H), 5.90(br.s, 1H), 6.80–6.95(m, 3H), 7.10–7.40(m, 3H), 7.40–7.80(AB-type, 4H) |
| 24 | 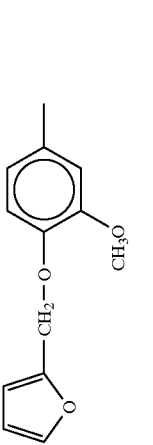 (furan-2-yl-CH₂-O- with CH₃ and OCH₃) | 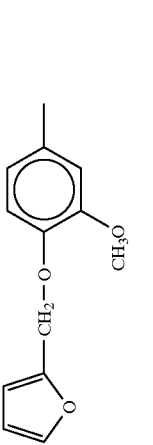 (2,6-di-tert-butyl-4-methylphenyl) | Colorless crystal (157–159) | 437 | 1.14(d, 12H), 3.05–3.55(m, 2H), 3.79(s, 3H), 4.10–4.70(m, 3H), 5.00(s, 2H), 6.20–6.40(m, 3H), 6.50–7.00(m, 3H), 7.00–7.50(m, 4H) |

-continued

| Compound No. | R³—(CH₂)ₙ—O—[Ar with R¹, R²] | R⁴ | Melting Point (°C) | MS (FAB, Pos.) | ¹H-NMR data (CDCl₃, δ) |
|---|---|---|---|---|---|
| 25 | O₂N—C₆H₄—CH₂—O—(2-CH₃, 4-CH₃-phenyl) | 2,6-di-tert-butyl-4-methylphenyl | Colorless crystal (195–196) | 476 | 1.14(d, 12H), 2.25(s, 3H), 3.28(m, 2H), 4.30(d, 2H), 4.43(br, 1H), 5.14(s, 2H), 5.75(s, 2H), 6.71(d, 1H), 6.98(d, 1H), 7.05(s, 1H), 7.17(d, 2H), 7.30(t, 1H), 7.59(d, 2H), 8.24(d, 2H) |
| 26 | O₂N—C₆H₄—CH₂—O—(2-CH₃, 5-Cl-phenyl) | 2,6-di-tert-butyl-4-methylphenyl | Colorless crystal (205–206) | 496 | 1.13(d, 12H), 3.26(m, 2H), 4.42(d, 2H), 4.66(br, 1H), 5.02(s, 2H), 5.84(s, 1H), 6.71(d, 1H), 7.15(dd, 1H), 7.16(d, 2H), 7.25(d, 1H), 7.29(t, 1H), 7.38(s, 2H), 8.19(d, 2H) |
| 27 | CH₃OOC—C₆H₄—CH₂—O—(2-OCH₃, 4-CH₃-phenyl) | 2,6-di-tert-butyl-4-methylphenyl | Colorless crystal (172–173) | 505 | 1.13(d, 12H), 3.10–3.50(m, 2H), 3.84(s, 3H), 3.91(s, 3H), 4.20–4.35(d, 2H), 4.35–4.60(t, 1H), 5.16(s, 2H), 5.97(br.s, 1H), 6.60–6.90((m, 3H), 7.05–7.40(m, 3H), 7.40–7.55(m, 2H), 7.90–8.10(m, 2H) |
| 28 | CF₃—C₆H₄—CH₂—O—(2-OCH₃, 4-CH₃-phenyl) | 2,6-di-tert-butyl-4-methylphenyl | Colorless crystal (164–166) | 515 | 1.13(d, 12H), 3.00–3.50(m, 2H), 3.84(s, 3H), 4.20–4.40(d, 2H), 4.40–4.60(t, 1H), 5.16(s, 2H), 6.02(br.s, 1H), 6.60–6.90(m, 3H), 7.05–7.40(m, 3H), 7.40–7.70(m, 4H) |

-continued

| Compound No. | R³—(CH₂)ₙ—O— (with R¹, R² on phenyl with CH₃) | R⁴ (2,6-di-tert-butyl-methylphenyl) | Melting Point (°C.) | MS (FAB, Pos.) | ¹H-NMR data (CDCl₃, δ) |
|---|---|---|---|---|---|
| 29 | 4-[C(CH₃)₂(CH₃)]-phenyl-CH₂-O- with 3-OCH₃ on tolyl | 2,6-di-t-Bu-methylphenyl | Colorless crystal (165–167) | 503 | 1.13(d, 12H), 1.31(s, 9H), 3.10–3.50(m, 2H), 3.82(s, 3H), 4.30–4.40(d, 2H), 4.40–4.60(t, 1H), 5.07(s, 2H), 5.95(br.s, 1H), 6.65–6.90(m, 3H), 7.05–7.50(m, 7H) |
| 30 | 4-CH₃O-phenyl-CH₂-O- with 3-OCH₃ on tolyl | 2,6-di-t-Bu-methylphenyl | Colorless crystal (163–164) | 461 | 1.13(d, 12H), 2.33(s, 3H), 3.05–3.50(m, 2H), 3.81(s, 3H), 4.20–4.40(d, 2H), 4.40–4.60(t, 1H), 5.06(s, 2H), 6.05(br.s, 1H), 6.60–6.85(m, 3H), 7.00–7.40(m, 7H) |
| 31 | 3-CH₃O-phenyl-CH₂-O- with 2-OCH₃ on tolyl | 2,6-di-t-Bu-methylphenyl | Colorless crystal (170–171) | 477 | 1.13(d, 12H), 3.10–3.50(m, 2H), 3.79(s, 3H), 3.83(s, 3H), 4.20–4.40(d, 2H), 4.40–4.60(t, 1H), 5.08(s, 2H), 6.09(br.s, 1H), 6.60–7.10(m, 6H), 7.10–7.40(m, 4H) |
| 32 | 2-thienyl-CH₂-O- with 3-OCH₃ on tolyl | 2,6-di-t-Bu-methylphenyl | Colorless crystal (158–161) | 453 | 1.14(d, 12H), 3.10–3.50(m, 2H), 3.81(s, 3H), 4.20–4.40(d, 2H), 4.40–4.60(t, 1H), 5.23(s, 2H), 5.99(br.s, 1H), 6.60–7.40(m, 9H) |

-continued

| Compound No. | R³—(CH₂)ₙ— with R¹/R² phenyl-O | R⁴ | Melting Point (°C.) | MS (FAB, Pos.) | ¹H-NMR data (CDCl₃, δ) |
|---|---|---|---|---|---|
| 33 | furan-2-yl-CH₂—O— phenyl(CH₃) | 2,6-di-t-butyl-methylphenyl | Colorless crystal (163–165) | 437 | 1.14(d, 12H), 3.10–3.50(m, 2H), 3.81(s, 3H), 4.20–4.40(d, 2H), 4.40–4.60(t, 1H), 4.96(s, 2H), 5.91(br.s, 1H), 6.40–6.90(m, 4H), 7.10–7.60(m, 5H) |
| 34 | HOOC-phenyl-CH₂—O— phenyl(CH₃O) | 2,6-di-t-butyl-methylphenyl | Colorless crystal (174–177) | 513 | 1.12(d, 12H), 3.00–3.40(m, 2H), 3.86(s, 3H), 4.20–4.45(d, 2H), 4.45–4.75(t, 1H), 5.18(s, 2H), 6.60–6.90(m, 3H), 7.00–7.20(m, 3H), 7.20–7.60(m, 2H), 7.00–8.00(br, 2H), 8.00–8.20(m, 2H) |
| 35 | phenyl-CH₂—O—phenyl(CH₃) | 2,6-di-t-butyl-methylphenyl | Colorless crystal (181–182) | 417 | 1.14(d, 12H), 3.00–3.50(m, 2H), 4.20–4.60(m, 3H), 5.01(s, 2H), 6.07(br.s, 1H), 6.80–7.50(m, 12H) |
| 36 | (CH₃)₂N-phenyl-CH₂—O—phenyl(CH₃) | 2,6-di-t-butyl-methylphenyl | Viscous colorless liquid | 460 | 1.05(d, 12H), 2.82(m, 2H), 2.95(s, 6H), 4.52(s, 4H), 4.55(br, 1H), 5.70(s, 1H), 6.65(dd, 1H), 6.71(d, 2H), 6.78(br.s, 1H), 6.81(d, 1H), 7.06(d, 2H), 7.13(t, 1H), 7.17(d, 2H), 7.17(t, 1H) |

Test Example 1

With respect to the compound (1) according to the present invention, the pharmacological effects were tested. The results are as follows.

i) Test for inhibitory activity against ACAT using J774 cells:

The ACAT activity of J774 cells was measured as the radioactivity of cholesteryl oleate produced from [$^{14}C$]oleic acid and cholesterol which were added to a culture solution.

More specifically, cultured J774 cells were plated on a 24 F culture plate containing a serum-free RPMI 1640 medium so as to account for $1 \times 10^{-6}$ cells/well. Added to the cells were [$^{14}C$]oleic acid, delipidized BAS (bovine serum albumin), reconstituted ribosome (0.3 M glucose solution containing cholesterol and phosphatidylcholine at a weight ratio of 2:1) and 25-hydroxycholesterol to culture the cells for 4 hours at 37° C. under 5% $CO_2$. After the culturing, the cultured cells were disrupted with a 1% SDS (sodium dodecyl sulfate) solution, and the lipid in the disrupted solution was extracted with hexane. The extract was dried to solid under reduced pressure. After the resultant residue was then developed (developing solvent: diethyl ether/hexane/acetic acid=80/20/1) by TLC (thin-layer chromatography), the amount of cholesteryl oleate formed was determined by an imaging plate.

A DMSO (dimethyl sulfoxide) solution of each specimen was added in an amount of 1% to the culture solution to find its inhibition rate against the enzymatic activity in comparison with a DMSO control.

TABLE 11

| Compound | Inhibition rate against ACAT activity in J774 cells (%) |
| --- | --- |
| Compound 1 | 86.29 ± 1.58 |
| TMP-153 | 36.94 ± 11.93 |
| Dup 128 | 66.37 ± 6.17 |

Tested on 100 nM of each compound.
(Mean ± S.D.; n = 3)
TMP-153 [H. Tawada et al., J. Med. Chem., 37, 2079–2084 (1994)]

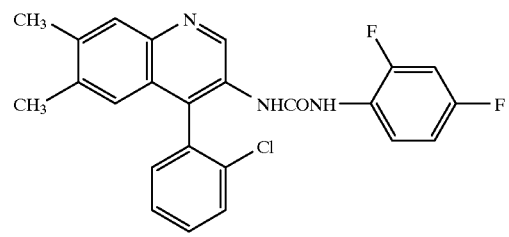

Dup 128 [T. P. Maduskuie, Jr., et al., J. Med. Chem., 38, 1067–1083 (1995)]

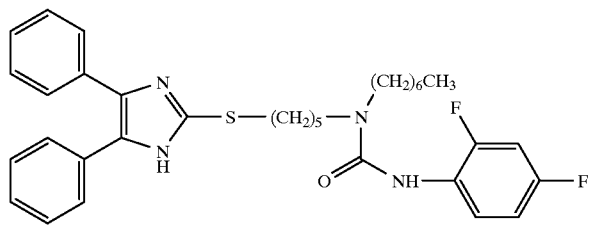

ii) Test for inhibitory activity against ACAT using rat liver microsomes:

The ACAT activity of rat liver microsomes was measured as the radioactivity of cholesteryl oleate produced from [$^{14}C$]oleoyl-CoA and endogenous cholesterol.

More specifically, [$^{14}C$]oleoyl-CoA and delipidized BSA were added to a rat liver microsome fraction prepared in accordance with a method known per se in the art to conduct a reaction at 37° C. for 5 minutes. After the reaction, the lipid in the reaction mixture was extracted with hexane, and the extract was dried to solid under reduced pressure. After the resultant residue was then developed (developing solvent: diethyl ether/hexane/acetic acid=80/20/1) by TLC, the amount of cholesteryl oleate formed was determined by an imaging plate. A DMSO solution of each specimen was added in an amount of 1% to the reaction mixture to find its inhibition rate against the enzymatic activity in comparison with a DMSO control.

TABLE 12

| Compound | Inhibition rate against ACAT activity in rat liver microsome (%) |
| --- | --- |
| Compound 1 | 0 |
| TMP-153 | 82.29 ± 2.79 |
| Dup 128 | 79.32 ± 7.01 |

Tested on 100 nM of each compound.
(Mean ± S.D.; n = 3)

As apparent from the results of the tests i) and ii), the compound (1) according to the present invention has still stronger inhibitory activity against ACAT in the mouse macrophage-like cells than against ACAT in the liver microsomes. This fact means that the compound according to the present invention directly reduces the accumulation and storage of cholesterol esters in the artery wall to prevent the formation or development of atherosclerosis lesion. Therefore, such a compound is useful in preventing and treating arteriosclerosis, and moreover various diseases related thereto, for example, cerebral infarction, transient ischemic attack, angina pectoris, peripheral thrombus and peripheral occlusion.

What is claimed is:

1. A substituted benzylurea derivative represented by the formula (1):

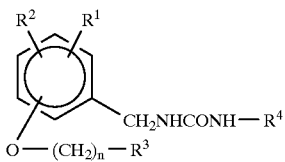

(1)

wherein $R^1$ and $R^2$ are the same or different from each other and independently represent a hydrogen atom, halogen atom, an alkyl group or alkoxyl group, $R^3$ is a phenyl furanyl, thienyl, or pyridyl group which may be substituted by a halogen atom, halogenated $C_{1-6}$ alkyl group, linear or branched $C_{1-6}$-alkoxyl group, mono- or di-$C_{1-6}$ alkylamino group, cyano group, carboxyl group, $C_{1-6}$-alkoxycarbonyl group, hydroxy group, nitro group, linear or branched $C_{1-6}$ alkyl group, hydroxy $C_{1-6}$-alkyl group or $C_{2-6}$ alkenyl group, n is an integer of 1–6, and $R^4$ is a di-isopropyl phenyl group, or a salt thereof.

2. The benzylurea or salt thereof according to claim 1, wherein $R^1$ and $R^2$ are the same or different from each other and are independently selected from the group consisting of hydrogen atom, halogen atom, linear or branched $C_{1-6}$ alkyl group, linear $C_{1-6}$ alkoxyl group and branched $C_{1-6}$ alkoxyl group; and $R^3$ is substituted by 1 to 3 substituents.

3. A pharmaceutical composition comprising a substituted benzylurea derivative or salt thereof according to claim 1 or 2 as an active ingredient and a pharmaceutically acceptable carrier.

4. The pharmaceutical composition according to claim 3, which is a prophylactic and therapeutic agent for arteriosclerosis.

5. A method of preventing and treating arteriosclerosis, which comprises administering an effective amount of the substituted benzylurea derivative or the salt thereof according to claim 1 or 2 to a human or mammal.

* * * * *